United States Patent [19]

Larkin et al.

[11] 4,036,866

[45] July 19, 1977

[54] PROCESS FOR RECOVERING ORGANOTIN HALIDES

[75] Inventors: William A. Larkin, Morristown; Alfred Stoloff, Livingston, both of N.J.

[73] Assignee: M & T Chemicals Inc., Greenwich, Conn.

[21] Appl. No.: 622,374

[22] Filed: Oct. 14, 1975

Related U.S. Application Data

[63] Continuation-in-part of Ser. No. 499,503, Aug. 22, 1974, Pat. No. 3,931,264.

[51] Int. Cl.$^2$ .............................................. C07F 7/22
[52] U.S. Cl. ................................................... 260/429.7
[58] Field of Search ..................................... 260/429.7

[56] References Cited

U.S. PATENT DOCUMENTS

| 2,569,492 | 10/1951 | Passino et al. | 260/429.7 |
|---|---|---|---|
| 3,297,732 | 1/1967 | Banks | 260/429.7 |
| 3,389,158 | 6/1968 | Kushlefsky | 260/429.7 |
| 3,404,167 | 10/1968 | Gray | 260/429.7 |
| 3,415,857 | 12/1968 | Hoye et al. | 260/429.7 |
| 3,519,665 | 7/1970 | Molt et al. | 260/429.7 |

*Primary Examiner*—Arthur P. Demers
*Attorney, Agent, or Firm*—Robert P. Auber; Kenneth G. Wheeless; Robert Spector

[57] ABSTRACT

Certain organotin halides can be recovered in substantially quantitative yield from aqueous media containing an ammonia or amine complex of these halides by adding (1) a non-reactive highly soluble inorganic salt to partially or completely saturate the solution and (2) an amount of a suitable mineral acid sufficient to decompose said complex and then heating the resultant solution as required to effect a separation of the resultant organotin halide from the aqueous phase.

11 Claims, No Drawings

/ 1

PROCESS FOR RECOVERING ORGANOTIN HALIDES

BACKGROUND

This application is a continuation-in-part of application Ser. No. 499,503, filed Aug. 22, 1974, now U.S. Pat. No. 3,931,264.

This invention relates to a method for recovering certain water-soluble organotin halides from aqueous solutions containing complexes of these organotin compounds with ammonia or an amine.

Organotin halides of the general formula $R_aSnX_{4-a}$ wherein each R represents a hydrocarbon radical, particularly a lower alkyl radical and X represents chlorine, bromine or iodine, and $a$ is 1, 2 or 3 are employed as biocides for controlling a variety of undesirable organisms and as auxiliary heat stabilizers for halogen-containing polymers. A major portion of the organotin halides produced are employed as intermediates for preparing organotin derivatives that are useful as catalysts, herbicides, insecticides, anti-microbial agents and for a variety of other applications in the agricultural, coating and chemical industries. For example, when applied to heated glassware such as bottles and other containers, organotin halides decompose to yield an adherent coating of stannic oxide on the glass. This is often the first step in forming conductive, protective or decorative coatings on glass containers.

Organotin halides are relatively costly and may exhibit a significant level of mammalian toxicity. It is therefore usually desirable to recover substantially all of these compounds either as products or unconverted starting material. The recovered organotin halides should be relatively pure.

Many of the lower alkyltin halides may be particularly difficult to recover in pure form. These compounds are volatile, corrosive liquids. Special precautions must be exercised during the processing and transporting of these materials. If allowed to come in contact with the skin or respiratory tract, the damaging effects are similar to those produced by hydrogen chloride.

It is reported in the chemical literature that organotin halides react with amines or anhydrous ammonia to yield solid complexes. These complexes are often in the form of fine, white powders that present none of the hazards associated with the free organotin halides. The complexes decompose readily in the presence of aqueous solutions of mineral acids, yielding the corresponding organotin halide. While the aforementioned complexes facilitate recovery and processing of organotin halides, the problem still remains of how to isolate a water-soluble organotin halide from the aqueous solution of a mineral acid that is employed to decompose the corresponding complex of the halide with ammonia or an amine. A conventional method for recovering water-soluble organotin halides from an aqueous solution is by distillation whereby a portion or all of the water is boiled off, leaving a residue of the desired organotin compound. If the organotin compound is present in combination with other water-soluble organotin compounds, the boiling points may differ sufficiently to permit separation of the organotin compounds by fractional distillation once the water is removed. Distillation may not be possible without significant loss of product if the boiling point of the organotin halide is close to that of water or if the organotin compound decomposes to any appreciable extent when heated to the temperature required to remove the water. Even if the desired separation can be effected by distillation, the process requires expensive equipment and considerable amounts of energy in the form of heat. In addition, the recovered organotin compound may require further processing to achieve the desired level of purity. Organotin halides that melt above ambient temperature can often be purified by recrystallization, however this requires an additional process step and the use of organic solvents. Since many of the organic solvents are flammable and/or volatile, they present a hazard to the safety and health of personnel handling these materials in addition to increasing manufacturing costs.

An objective of this invention is to provide a simple, relatively low cost method for recovering a number of the water-soluble organotin halides in relatively pure form and high yield from aqueous media containing a complex of these compounds with ammonia or an amine. It has now been found that this objective can be achieved by adding to the aqueous medium containing these water-soluble complexes a sufficient amount of acid to completely decompose the complex and a strong inorganic electroylte in an amount sufficient to form a partially or completely saturated solution at ambient temperature, and then heating the resultant solution to effect a separation of the organotin halide.

SUMMARY OF THE INVENTION

This invention provides a method for isolating a liquid or solid organotin halide of the formula $(CH_3)_aSnX_{4-a}$ or $C_4H_9SnX_3$ in substantially pure form from an aqueous medium containing more than about 55% by weight of said organotin halide in the form of a water-insoluble complex with ammonia or an amine, the method consisting essentially of the following sequence of steps:

1. combining with said aqueous solution (a) an amount of a water-soluble inert inorganic salt sufficient to attain a concentration of from 50 g. of said salt per 100 cc. of water up to the concentration equivalent to a saturated solution of said salt, and (b) a non-oxidizing mineral acid in an amount sufficient to completely decompose said complex;

2. heating the resultant solution to a temperature between ambient and the boiling point of the solution to effect a separation of the organotin halide from the aqueous phase;

3. isolating the organotin halide.

In the foregoing formula $a$ is the integer 2 or 3 and X represents chlorine, bromine or iodine.

DETAILED DESCRIPTION OF THE INVENTION

The present method for separating amine complexes of certain water-soluble organotin halides from an aqueous solution resembles the technique known as "salting out", whereby a strong electrolyte, usually a high soluble salt of a polyvalent metal, is added to an aqueous solution containing a solubilized weak electrolyte for the purpose of precipitating the latter from the solution as an immiscible liquid or solid. A separation of the organotin halide from the aqueous phase containing the inorganic salt is achieved by heating the solution. In this respect the present method differs from the conventional "salting out", which is usually conducted at or below ambient temperature. Once separated from the aqueous phase, the halide is readily isolated by conventional methods, which include decantation and filtration. Since the solubility of the inorganic electrolyte usually increases as the temperature is raised, it is unlikely that any of the electrolyte will precipitate from the solution along with the organotin halide.

Using the present technique it is feasible to recover at least 65% of the organotin halides present in an aqueous solution.

While the present method is operable using complexes of di- or trimethyltin halides and butyltin trihalides, the corresponding ethyltin halides cannot be precipitated by this method. This is surprising and unexpected.

In accordance with the present method complexes of organotin halides with ammonia or amines are decomposed by reacting the complexes with an aqueous solution of a mineral acid. Any of the known mineral acids except strongly oxidizing acids such as nitric acid can be employed for this purpose. Since some acids are known to form relatively stable compounds with organotin halides that may interfere with the precipitation of these halides in the presence of strong electrolytes, the number of equivalents of acid added whould be stoichiometrically equal to the number of equivalents of amine or ammonia that are complexed with the organotin halide. This will ensure that substantially no free acid is present following decomposition of the complex.

Suitable mineral acids include hydrochloric, hydrobromic, sulfuric, phosphoric and perchloric acids.

To minimize the number of processing steps required to isolate the present organotin halides, the mineral acid and the aforementioned strong electrolyte are preferably present in the same solution. The complex is decomposed and the resultant organotin halide precipitated from the same liquid medium. Many neutralization products of the mineral acid and the amine or ammonia liberated upon decomposition of the complex remains in solution and would not interfere with the subsequent recovery of the organotin halide. If the neutralization product is insoluble, it can readily be removed by conventional techniques such as filtration before the reaction mixture is heated to recover the organotin halide. Most preferably the mineral acid selected is one which forms a water-soluble reaction product with the amine that is complexed with the organotin halide. Hydrochloric acid is preferred among those mineral acids yielding water-soluble decomposition products.

All of the present organotin halides can be isolated from their aqueous solution when present at a concentration greater than about 55% by weight. If a given solution is too dilute for an effective separation using the present method, some of the water should be removed by distillation, which is preferably conducted under reduced pressure to avoid or at least minimize heat-induced decomposition of the organotin compound.

Depending upon the solubility of the organotin halide in water, the mimimum concentration of inorganic salt necessary to completely precipitate the organotin halide is between 50 and 130% or more of the amount theoretically equivalent to a saturated solution of the salt at ambient temperature. Some salts will form supersaturated solutions under certain conditions, which would account for a solubility higher than the theoretical maximum.

The present method of isolating organotin halides from an aqueous solution of inorganic salts differs from a conventional salting out of weak electrolytes in that once the organotin compound separates from a heated saturated solution it does not redissolve when the solution is cooled to ambient temperature. The precipitation of weak electrolytes from aqueous solution is usually a reversible reaction, in that once the second phase forms it can be redissolved by adjusting the concentration of strong electrolyte, the temperature of the aqueous phase or both to levels at which a single phase exists.

Inorganic salts suitable for precipitating the present organotin halides do not react with the organotin halide and are soluble at ambient temperature to the extent of at least about 50 g. per 100 cc. of water. Of the salts which meet these two criteria, preferred ones include the chlorides, bromides and iodides of zinc, calcium and manganese.

Other suitable readily available inorganic salts include, but are not limited to,
ammonium bromate
ammonium iodide
barium bromide
barium iodide
calcium nitrate
ferric halides
lead acetate
lithium bromide
magnesium acetate
nickel halides
potassium acetate
potassium carbonate
potassium fluoride
potassium iodide
sodium iodide
strontium bromide
strontium iodide The concentration of salt necessary to completely precipitate the organotin halide will vary depending upon the solubility of the organotin halide. Salt concentrations greater than 50 g per 100 cc. of water are usually required to recover more than about 50% of the organotin halide. For the more soluble halides, such a dimethyltin dichloride, a saturated or super-saturated solution of the salt, equivalent to at least 200 g. of salt per 100 cc. of water, may be required to recover more than about 90% of the organotin compound.

The inorganic salt should be anhydrous to minimize the amount of salt required to precipitate the organotin compound. Some hydrated salts such as ferric chloride hexahydrate contain nearly equal amounts of salt and water. These hydrated salts are therefore too inefficient for use in the present method due to the inordinately large amount required to attain the desired concentration of salt in the solution.

Complexes of organic and inorganic tin halides with ammonia or amines are readily prepared by combining the halide with the complex-forming reagent. When the reagents are in the vapor phase, the reaction is instantaneous, for all practical purposes at ambient temperatures, however it may be desirable to maintain the reagents in contact with one another for several minutes to ensure a complete reaction. For reactions employing a liquid phase, the temperature of the reaction mixture is preferably between 20° and 100° C. Since the reaction is usually exothermic, no external heating may be required. The solid complex precipitates in the reaction chamber or vessel, often as a finely divided white powder. In those instances when the amine is a liquid the reaction with the organotin halide can either be carried out "neat", i.e. without any diluent, or in the presence of a suitable inert organic liquid such as n-hexane, benzene or toluene.

The present organotin halides will react with virtually all primary, secondary and tertiary amines wherein the nitrogen atom is not so hindered as to prevent an association between the nitrogen atom of the amine and the organotin halide.

Amines suitable for use in preparing water-insoluble adducts with the present organotin halides are primary, secondary and tertiary amines wherein the hydrocarbon radicals bonded to the nitrogen atom contain between 1 and 20 carbon atoms. Representative amines include methylamine, dimethylamine, n-propyl amine and structural isomers thereof, aniline and heterocyclic amines such as pyridine. To be useful in the present method for recovering organotin halides the salt formed following dissociation of the organotin halide-amine complex with aqueous acid should preferably be soluble in water. If the salt is not soluble in water it will precipitate together with the organotin halide when the complex is added to an acidified aqueous solution of an inorganic salt. Separation of the salt from the organotin halide would require an additional filtration or decantation step to separate the salt, thereby increasing the cost of the recovery process.

As previously disclosed, when it is desired to recover the organotin halide from the complex, the latter is combined with water containing sufficient acid to decompose the complex and liberate the organotin halide. The inorganic salt to be employed for precipitating the halide can either be present in the aforementioned aqueous acid solution or is added following decomposition of the complex.

The following example demonstrates preferred embodiments of the present method and demonstrates that the method cannot be employed with organotin halides that are not within the scope of the invention as defined in the accompanying claims. All parts and percentages are by weight.

EXAMPLE 1

This example demonstrates the preparation and decomposition of an ammonia complex of butyltin trichloride and the recovery of the resultant organotin halide from aqueous solution.

A reservoir containing butyltin trichloride was heated to 120° C. The resultant vapor was entrained in a stream of nitrogen and directed into a 2 liter capacity glass reaction vessel. When gaseous anhydrous ammonia was admitted into this reaction vessel a finely divided white precipitate formed and the wall of the reaction vessel became hot. Upon analysis the white precipitate was found to contain 33.0% by weight of tin, 9.9% nitrogen, 13.6% carbon, 5.8% hydrogen and 29.5% chlorine. The calculated analysis for a complex of the formula $C_4H_9SnCl_3.3NH_3$ is 35.7% tin, 12.6% nitrogen, 14.4% carbon, 5.4% hydrogen and 32.1% chlorine.

The complex was decomposed by gradually adding a 90 g. portion of the complex to an aqueous solution containing 200 g. of water, 400 g. of calcium chloride dihydrate and 90 g. of concentrated (12 normal) aqueous hydrochloric acid. The resultant mixture was heated to a temperature of 115° C. The solution was stirred during the addition of the complex. Stirring was continued until the complex was completely reacted, which required between 15 and 30 minutes. Butyltin trichloride precipitated from the reaction mixture as an immiscible liquid and was recovered using a separatory funnel. The recovered butyltin trichloride weighed 67 g., which is equivalent to a yield of 88%, based on the weight of organotin halide present in the original complex.

EXAMPLE 2

This example demonstrates the preparation of a pyridine-butyltin trichloride complex.

A 14.6 g. (0.2 mole) portion of pyridine was added gradually to a stirred solution containing 28.2 g. (0.1 mole) of butyltin trichloride and 100 g. of benzene. Heat was evolved and a white precipitate formed. Stirring was continued for about five minutes, following which the complex was isolated, washed with benzene and then dried at 50° C. under reduced pressure for one hour. The dried material weighed 40 g., which is equivalent to a 93% yield, based on the weight of butyltin trichloride. Upon analysis the solid was found to contain 26.49% by weight of tin, 24.32% chlorine and 6.35% nitrogen. This analysis corresponds to the formula $C_4H_9SnCl_3.2C_5H_5N$.

A methyltin trichloride-pyridine complex was prepared as described in the first part of this example using 22 g. of methyltin trichloride, 15.8 g. of pyridine and 100 cc. of benzene.

EXAMPLE 3

This example demonstrates the decomposition of various organotin halide-amine complexes and recovery of the corresponding organotin halide from an aqueous medium.

A 1.0 g. sample of various complexes containing dimethyltin dichloride or butyltin trichloride was added with stirring to 7 cc. of an aqueous solution containing 33% by weight of calcium chloride dihydrate. A 1 cc. portion of concentrated (12N) aqueous hydrochloric acid was added to each 7 cc. portion of salt solution prior to addition of the complex. The resultant mixture was heated to 100° C. and maintained at that temperature for 5 minutes. The mixture was then allowed to cool and the temperature at which a separation of phases occurred was noted and is recorded in the following table together with the physical appearance of the lower phase.

| Complex Components | | Temperature of Phase Separation (° C.) | Separated Phase |
|---|---|---|---|
| Halide | Amine | | |
| $C_4H_9SnCl_3$ | $NH_3$ | 75 | Oil |
| $C_4H_9SnCl_3$ | $C_5H_5N$ | 95 | Oil |
| $(CH_3)_2SnCl_2$ | $(CH_3CH_2)_2NH$ | 90 | Solid |
| $(CH_3)_2SnCl_2$ | $C_5H_5N$ | 75 | Solid |
| $(CH_3)_2SnCl_2$ | $NH_3$ | <21 | Solid |

EXAMPLE 4

The solubility in water of various organotin chlorides and an organotin bromide containing between one and eight carbon atoms was investigated using 10 parts or 55 parts of the organotin halide for each 100 parts of water. The mixture was then heated to 100° C. to determine whether the solubility of the halide at 100° C. differed from the value at 21° C. The results are summarized in the following table. Soluble compounds are indicated by the letter s, unsoluble compounds by the letter i.

TABLE I

| COMPOUND | PARTS OF COMPOUND 100 PARTS WATER | SOLUBILITY AT 21° C. | AT 100° C. |
| --- | --- | --- | --- |
| $CH_3SnCl_3$ | 10 | s | s |
|  | 55 | s | s |
| $(CH_3)_2SnCl_2$ | 10 | s | s |
|  | 55 | s | s |
| $(CH_3)_3SnCl$ | 10 | s | s |
|  | 55 | s | s |
| $C_2H_5SnCl_3$ | 50 | s | s |
| $(C_2H_5)_2SnBr_2$ | 50 | i | i |
| $C_4H_9SnCl_3$ | 10 | s | s |
|  | 55 | s | s |
| $(C_6H_5)_2SnCl_2$ | 10 | i | i |
| $C_8H_{17}SnCl_3$ | 10 | i | i |
| $(C_4H_9)_2SnCl_2$ | 10 | i | i |

An attempt was made to precipitate those organotin halides which dissolved using aqeous solutions of calcium chloride were employed at each of the three temperatures. The concentration of the various solutions were as follows:

| Solution No. | Temperature of Solution | Grams of $CaCl_2 \cdot 2H_2O$ per 100 cc. of water |
| --- | --- | --- |
| 1 | 21° C. | 79.62 |
| 2 | 21° C. | 99.53 |
| 3 | 21° C. | 129.39 |
| 4 | 70° C. | 151.44 |
| 5 | 70° C. | 189.30 |
| 6 | 70° C. | 246.10 |
| 7 | 100° C. | 169.9 |
| 8 | 100° C. | 212.4 |
| 9 | 100° C. | 276.1 |

A 2 cc. portion of each of the nine organotin halide solutions listed in Table I was added to an 8 cc. portion of each of the nine calcium chloride solutions, which were then heated to the temperature specified in the following Table 2 and maintained at that temperature for 5 minutes. The percent by weight of the organotin halide present in the solution appears immediately below the formula for the organotin compound. The type of second phase which formed, if any, is noted. The absence of any entry indicates that only one phase was present.

TABLE 2

| Temp. of Solution °C. | CaCl2 Soln. No. | (control) $CH_3SnCl_3$ | | $(CH_3)_2SnCl_2$ | | $(CH_3)_3SnCl$ | | (control) $C_2H_5SnCl_3$ | $C_4H_9SnCl_3$ | |
| --- | --- | --- | --- | --- | --- | --- | --- | --- | --- | --- |
|  |  | 10% | 55% | 10% | 55% | 10% | 55% | 50% | 10% | 55% |
| 21 | 1 | — | — | — | slight ppt. | slight ppt. | gel | — | slight ppt. | — |
| 21 | 2 | — | — | — | heavy ppt. | slight ppt. | slight | — | slight ppt. | slight oil |
| 21 | 3 | — | — | — | heavy ppt. | ppt. | oil | — | slight oil | slight oil |
| 70 | 4 | — | — | — | heavy ppt. | ppt. | oil | — | — | heavy oil |
| 70 | 5 | — | — | — | heavy ppt. | — | oil heavy | — | — | heavy oil |
| 70 | 6 | — | — | — | heavy ppt. | — | oil heavy | — | — | heavy oil |
| 100 | 7 | — | — | — | heavy ppt. | — | oil heavy | — | — | heavy oil |
| 100 | 8 | — | — | — | heavy ppt. | — | oil heavy | — | heavy oil | heavy oil |
| 100 | 9 | — | — | — | heavy ppt. | — | oil heavy | — | heavy oil | heavy oil |

The data in Table 2 demonstrate that while methyltin trichloride and ethyltin trichloride are soluble in water, they cannot be recovered using the present method, which, for all practical purposes, is limited to organotin halides containing 2 or 3 methyl radicals or one butyl radical. Certain asymmetric organotin halides, such as methyl ethyltin dihalides and methyl propyltin dihalides may be recoverable from aqueous solutions using the present technique, however these compounds are either highly toxic or so difficult to prepare that they are of limited commerical interest.

What is claimed is:

1. A method for isolating an organotin halide of the general formula $(CH_3)_aSnX_{4-a}$ or $C_4H_9SnX_3$, wherein $a$ is the integer 2 or 3 and X represents chlorine, bromine or iodine, in substantially pure form from an aqueous medium containing more than about (55%) by weight of said organotin halide in the form of a water-insoluble complex with ammonia or an amine, the method consisting essentially of the following steps:
    1. combining said aqueous medium with (a) an amount of a chemically inert water-soluble, inorganic salt sufficient to attain a concentration of from 50 g. of said salt per 100 cc. of water up to the concentration equivalent to a saturated or supersaturated solution of said salt, and (b) a non-oxidizing mineral acid in an amount sufficient to completely decompose said complex;
    2. heating the resultant solution to a temperature between ambient and the boiling point of the solution as required to effect a separation of the organotin halide from the aqueous phase;
    3. isolating the organotin halide.
2. A method as described in claim 1 wherein X is chlorine.
3. A method as described in claim 1 wherein the water-soluble inorganic salt is a halide of calcium, zinc or manganese.
4. A method as described in claim 3 wherein the halide is a chloride.
5. A method as described in claim 4 wherein the chloride is calcium chloride.
6. A method as described in claim 1 wherein the concentration of said inorganic salt is equivalent to a saturated solution of said salt in the presence of the organotin halide.
7. A method as described in claim 1 wherein the complex contains said organotin halide and ammonia.
8. A method as described in claim 1 wherein said amine is selected from the group consisting of primary, secondary and tertiary alkylamines.
9. A method as described in claim 1 wherein said amine is a heterocyclic amine.
10. A method as described in claim 1 wherein said amine is pyridine.
11. A method as described in claim 1 wherein said mineral acid is hydrochloric acid.

* * * * *